US010512968B2

(12) United States Patent
Ogura et al.

(10) Patent No.: US 10,512,968 B2
(45) Date of Patent: Dec. 24, 2019

(54) METHOD FOR MANAGING CASTING PROCESS BASED ON PROPERTIES OF MOLDING SAND

(71) Applicant: Sintokogio, Ltd., Aichi (JP)

(72) Inventors: Yuichi Ogura, Aichi (JP); Tsuyoshi Sakai, Aichi (JP); Hisashi Harada, Aichi (JP)

(73) Assignee: SINTOKOGIO, LTD., Aichi (JP)

( * ) Notice: Subject to any disclaimer, the term of this patent is extended or adjusted under 35 U.S.C. 154(b) by 47 days.

(21) Appl. No.: 15/554,395

(22) PCT Filed: Jun. 8, 2015

(86) PCT No.: PCT/JP2015/066457
§ 371 (c)(1),
(2) Date: Aug. 29, 2017

(87) PCT Pub. No.: WO2016/143150
PCT Pub. Date: Sep. 15, 2016

(65) Prior Publication Data
US 2018/0056375 A1    Mar. 1, 2018

(30) Foreign Application Priority Data
Mar. 10, 2015 (JP) .................. 2015-046851

(51) Int. Cl.
*B22C 9/02* (2006.01)
*B22C 19/04* (2006.01)
(Continued)

(52) U.S. Cl.
CPC .................. *B22C 9/02* (2013.01); *B22C 5/00* (2013.01); *B22C 5/16* (2013.01); *B22C 9/00* (2013.01);
(Continued)

(58) Field of Classification Search
CPC .... B22C 5/00; B22C 5/16; B22C 9/00; B22C 9/02; B22C 19/04; B22D 47/02
(Continued)

(56) References Cited

U.S. PATENT DOCUMENTS 5,054,538 A    10/1991 Ibsen
5,589,650 A    12/1996 Flemming et al.
(Continued)

FOREIGN PATENT DOCUMENTS

EP    1 025 927 A1    8/2000
JP    3-77767    4/1991
(Continued)

OTHER PUBLICATIONS

Chinese Office Action issued in corresponding Chinese Application No. 201580074501.7, dated Sep. 5, 2018.
(Continued)

*Primary Examiner* — Kevin P Kerns
(74) *Attorney, Agent, or Firm* — Finnegan, Henderson, Farabow, Garrett & Dunner, LLP

(57) ABSTRACT

A method for managing a casting process based on measured properties of molding sand is provided so that casting defects or energy used can be reduced by changing the molding conditions for the mold to be produced or changing the steps after molding. The method for managing a casting process based on the properties of the molding sand includes a step (1) of measuring the properties of the molding sand just before the molding sand is supplied to a molding machine (40) and a step (2) of determining if the measured properties of the molding sand comply with predetermined properties so as to then switch between a step of molding a mold when the measured properties do comply with the (Continued)

predetermined properties and a step of molding a mold when the measured properties do not comply with the predetermined properties.

9 Claims, 4 Drawing Sheets

(51) Int. Cl.
    *B22C 5/16*     (2006.01)
    *B22D 47/02*     (2006.01)
    *B22C 5/00*     (2006.01)
    *B22C 9/00*     (2006.01)
    *G01N 33/24*     (2006.01)
    *G05B 1/00*     (2006.01)
    *G05B 13/02*     (2006.01)
    *G01N 33/205*     (2019.01)

(52) U.S. Cl.
    CPC .............. *B22C 19/04* (2013.01); *B22D 47/02* (2013.01); *G01N 33/24* (2013.01); *G01N 33/246* (2013.01); *G05B 1/00* (2013.01); *G05B 13/0265* (2013.01); *G01N 33/205* (2019.01)

(58) Field of Classification Search
    USPC ......................................................... 164/456
    See application file for complete search history.

(56) References Cited

U.S. PATENT DOCUMENTS 6,272,932 B1     8/2001     Nishida
6,470,953 B1    10/2002    Hirata et al.

FOREIGN PATENT DOCUMENTS

| | | |
|---|---|---|
| JP | 2001-321892 | 11/2001 |
| JP | 2009-166097 | 7/2009 |
| JP | 5397778 B2 | 1/2014 |
| WO | WO 2013-187341 A1 | 12/2013 |

OTHER PUBLICATIONS

Wuchi, Shi, "Green Molding Sand Quality Control in Volume Production", 2018 China Academic Journal Electronic Publishing House (2018).

Supplementary European Search Report dated Nov. 13, 2018 by the European Patent Office in corresponding European Patent Application No. 15884636.0.

METHOD FOR MANAGING CASTING PROCESS BASED ON PROPERTIES OF MOLDING SAND

TECHNICAL FIELD

The present invention relates to a method for managing a casting process based on the properties of the molding sand that is used for molding.

BACKGROUND ART

Conventionally, molding sand that is used for molding is mulled by a sand muller and then transported to a molding machine to be molded there. During that transportation or stationary pause before the sand is to be molded the properties of the molding sand change. That change in the properties affects the molding characteristics. Thus it may cause a casting defect. Thus a device has been developed for automatically sampling the molding sand just before it is to be supplied to a molding machine and for automatically measuring the properties of the molding sand. Its technology has been publicly known (for example, see Japanese Patent No. 5397778).

The data on the properties of the molding sand that are measured by that device are used to analyze, as historical data, a possible cause of a casting defect in the process for producing a cast product. However, the data are not used for changing molding conditions of a mold to be produced or for any process after molding. Thus the possibility of a casting defect may not be reduced or no energy may be saved. This is a problem.

In view of this problem, the purpose of the present invention is to provide a method for managing a casting process based on properties of molding sand, by which, based on the measured properties of the molding sand, the molding conditions of a mold to be produced or any process after molding can be changed so as to reduce the possibility of a casting defect or to save energy.

Another purpose of the present invention is to provide a method for managing a casting process by which data on the measured properties of the molding sand can be fed back to determine if the properties of the molding sand are appropriate, based on the quality of the cast product that is cast by using the molding sand.

SUMMARY OF INVENTION

To achieve the above-mentioned purposes, a method for managing a casting process based on properties of molding sand of the present invention comprises a step of measuring the properties of the molding sand just before the molding sand is supplied to a molding machine. It also comprises a step of determining if the measured properties of the molding sand comply with predetermined properties. If by the step of determining it is found that the measured properties do not comply with the predetermined properties, a mold is molded to have less strength than that of a mold that is molded by using molding sand whose properties do comply with the predetermined properties.

By the method for managing the casting process based on the properties of the molding sand of the present invention the properties of the molding sand include one or more features that are selected from a group of compressive strength, tensile strength, shear strength, water content, permeability, compactability, and a temperature, of the molding sand.

By the method for managing the casting process based on the properties of the molding sand of the present invention the mold that has been molded when by the step of determining it is found that the measured properties do not comply with the predetermined properties, and that has less strength than that of a mold that is molded by using molding sand whose properties do comply with the predetermined properties, is assembled at a step that comes after a step of molding. No molten metal is poured into the assembled mold.

By the method for managing the casting process based on the properties of the molding sand of the present invention, the mold that has been molded when by the step of determining it is found that the measured properties do not comply with the predetermined properties, and that has less strength than that of a mold that is molded by using molding sand whose properties do comply with the predetermined properties, is transported after being molded and is shaken out without molten metal being poured.

A method for managing a casting process based on properties of molding sand of the present invention comprises a step of measuring the properties of the molding sand just before the molding sand is supplied to a molding machine. It also comprises a step of determining if the measured properties of the molding sand comply with predetermined properties. If by the step of determining results that show that the measured properties do not comply with the predetermined properties continue at predetermined cycles, then the molding sand that is estimated to have the same properties is passed to a step of preparing sand, where the sand is mulled without being molded.

The method for managing the casting process based on the properties of the molding sand of the present invention further comprises a step of storing data on the measured properties of the molding sand as data on a cast product that has been produced by pouring molten metal into a mold that is molded by using that molding sand, if by the step of determining it is found that the measured properties do comply with the predetermined properties.

By the method for managing the casting process based on the properties of the molding sand of the present invention, in the step of storing data on the measured properties data on molding conditions by which the molding sand is molded are also stored as data on the cast product.

By the method for managing the casting process based on the properties of the molding sand of the present invention, the properties of the molding sand include one or more features that are selected from a group of compressive strength, tensile strength, shear strength, water content, permeability, compactability, and a temperature, of the molding sand. If in the step of determining it is found that one of the selected features exceed predetermined ranges, then the properties of the molding sand are determined not to comply with the predetermined properties. The method further comprises a step of modifying the predetermined ranges that are used in the step of determining based on the properties of the molding sand that are stored as data on the cast product, if quality of the cast product that has been produced does not comply with predetermined quality.

By the method for managing the casting process based on the properties of the molding sand of the present invention the properties of the molding sand include compressive strength, water content, and compactability. In the step of determining if the compressive strength, or the water content, or the compactability exceeds a predetermined range, then the measured properties of the molding sand are determined not to comply with predetermined properties.

ADVANTAGEOUS EFFECTS OF INVENTION

The present invention is a method for managing a casting process based on properties of molding sand that comprises the steps of measuring the properties of the molding sand just before the molding sand is supplied to a molding machine, and of determining if the measured properties of the molding sand comply with predetermined properties. If by the step of determining it is found that the measured properties do not comply with the predetermined properties, then a mold that is molded by using the molding sand has less strength than that of a mold that is molded by using the molding sand whose properties comply with the predetermined properties. Thus the present invention has various advantageous effects. They include reducing the possibility of a casting defect or saving energy, by changing the molding conditions of a mold to be produced or changing any process after molding, based on the measured properties of the molding sand.

By the present invention the method further comprises the steps of storing data on the measured properties of the molding sand as data on a cast product that has been produced by pouring molten metal into a mold that has been molded by using that molding sand, if, by the step of determining, it is found that the measured properties do comply with the predetermined properties. It further comprises the step of modifying the predetermined ranges that are used in the step of determining, based on the properties of the molding sand that are stored as data on the cast product, that the quality of the cast product that has been produced does not comply with the predetermined quality. Thus the present invention has various advantageous effects. They include the reliable determination that the properties of the molding sand are appropriate, by feeding back the data on the measured properties of the molding sand, if the cast product is defective, so as to modify the predetermined ranges that are used for determining if the properties of the molding sand are appropriate.

The basic Japanese patent application, No. 2015-046851, filed Mar. 10, 2015, is hereby incorporated by reference in its entirety in the present application.

The present invention will become more fully understood from the detailed description given below. However, the detailed description and the specific embodiments are only illustrations of the desired embodiments of the present invention, and so are given only for an explanation. Various possible changes and modifications will be apparent to those of ordinary skill in the art on the basis of the detailed description.

The applicant has no intention to dedicate to the public any disclosed embodiment. Among the disclosed changes and modifications, those which may not literally fall within the scope of the present claims constitute, therefore, a part of the present invention in the sense of the doctrine of equivalents.

The use of the articles "a," "an," and "the" and similar referents in the specification and claims are to be construed to cover both the singular and the plural form of a noun, unless otherwise indicated herein or clearly contradicted by the context. The use of any and all examples, or exemplary language (e.g., "such as") provided herein is intended merely to better illuminate the invention, and so does not limit the scope of the invention, unless otherwise stated.

DESCRIPTION OF EMBODIMENTS

Below the embodiments of the present invention are discussed with reference to the drawings. The term "casting process" means a process that is carried out within a system for producing a cast product. The process is carried out by a casting line that includes a line for preparing foundry sand, which line prepares molding sand that is used for molding. The casting line also includes a line for molding. It also includes a line for pouring molten metal into molds that have been molded in the line for molding.

Figure 1:
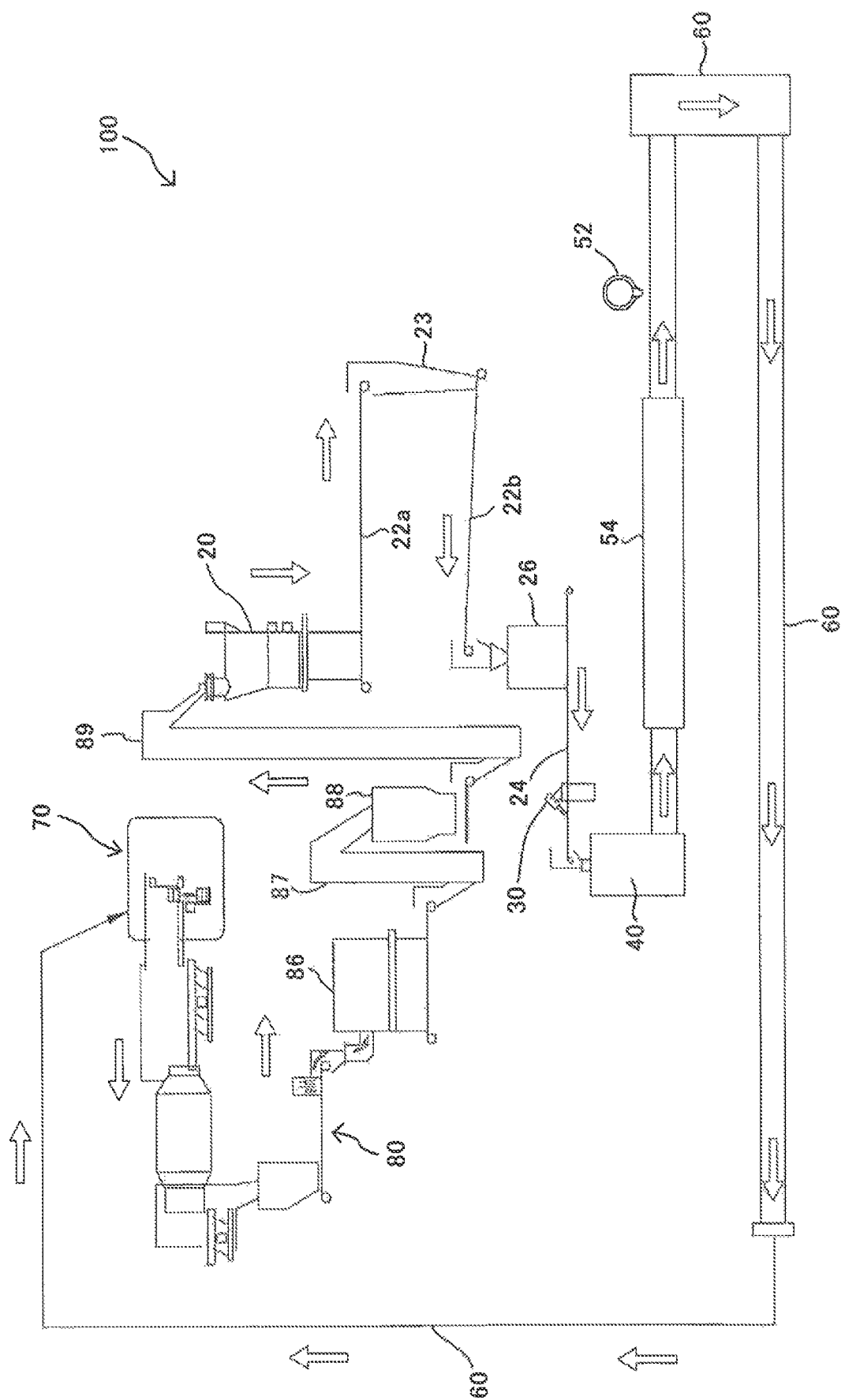
FIG. 1 is a schematic diagram of the configuration of the green sand casting system that is used for carrying out the present invention.

First, the casting system is discussed with reference to FIG. 1. FIG. 1 is a schematic drawing of the entire configuration of the green sand casting system 100. The term "green sand" indicates that a mold is produced by using green sand. It is used in contrast to the term "self-hardening." In the green sand casting system the location for mulling is separate from the location for molding. The molding sand that has been mulled by means of a sand muller 20 is transported to a molding machine 40 by means of a conveyor belt 22a, a hopper 23, a conveyor belt 22b, a device 26 for storing the molding sand, a conveyor belt 24, etc. Thus, even though the molding sand has been adjusted for molding, the properties of the sand may have changed, because water is evaporated during the transportation, etc.

In the conveyor belt 24 that is located downstream, a device 30 for measuring the properties of the molding sand is provided. It samples the molding sand to be fed to the molding machine 40 and measures the properties of the molding sand. By the device 30 for measuring the properties of the molding sand, the molding sand as it is just before being fed to the molding machine 40 can be automatically sampled, so that the properties are measured. The data on the measured properties are sent to the controller (not shown) that controls the operation of the green sand casting system 100.

Figure 2:
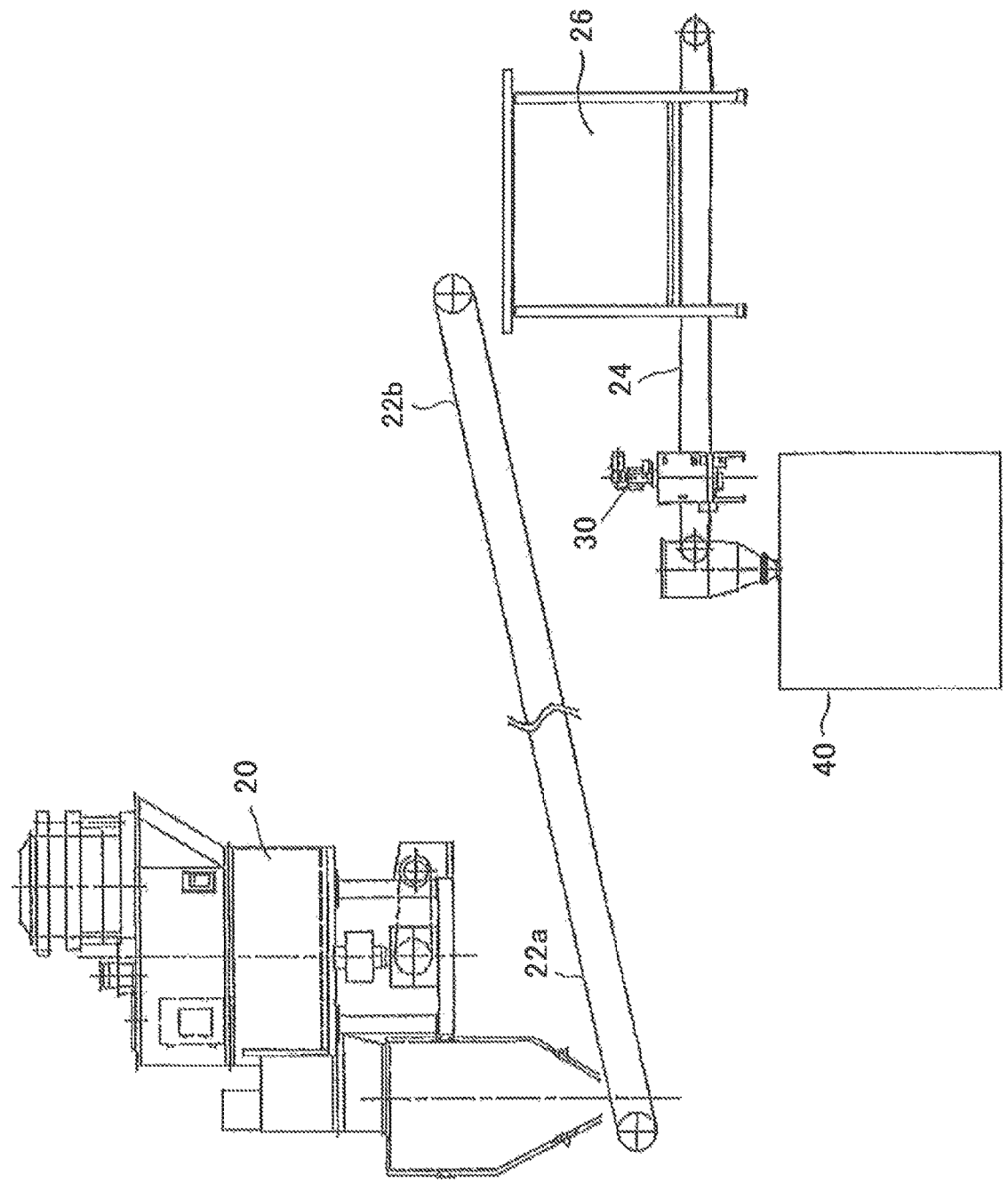
FIG. 2 is a schematic diagram of an example of a system that maintains machines that range from a mulling machine to a molding machine.

An example of the configuration of the device 30 for measuring the properties of the molding sand is shown in FIG. 2. By the green sand casting system as in FIG. 2 the molding sand that has been mulled by means of the sand muller 20 is transported by means of the conveyor belts 22a, 22b, the hopper 23, etc. Then it is stored in the device 26 for storing the molding sand. The device 26 for storing the molding sand is a hopper for temporarily storing the molding sand that is to be fed to the molding machine 40. The molding sand that is stored in the device 26 for storing the molding sand is fed to the molding machine 40 by means of the conveyor belt (a sand-feeder) 24. The device 30 for measuring the properties of the molding sand samples the molding sand, which has been stored in the device 26 for storing the molding sand, on the conveyor belt 24 to measure the properties of the molding sand.

A sprue is formed by means of a device for forming a sprue (not shown) of a device 54 for pretreatment to pour molten metal into a mold. The sprue is formed in an upper mold of the mold that has been produced by means of the molding machine 40. Next, a gas vent is formed in the upper mold by means of a device for forming a gas vent (not shown) of the device 54 for pretreatment to pour molten metal into a mold. Next, a core is set in an upper mold or a lower mold by means of a device for setting a core (not shown) of the device 54 for pretreatment to pour molten metal into a mold or by an operator. Next, a chiller or an exothermic material is set in an upper mold or a lower mold by means of a device for setting a chiller and setting an exothermic material (not shown) of the device 54 for pretreatment to pour molten metal into a mold, or by an operator. Next, the upper mold and the lower mold are assembled by means of a device for a mold assembly (not shown) of the device 54 for pretreatment to pour molten metal into a mold.

Molten metal is poured by means of a pouring machine 52 into the mold that has been assembled. The mold that has received molten metal is transported by means of a system 60 for transporting and cooling the molds that is structured by combining devices for transportation. By the system 60 for transporting and cooling the molds the molds are cooled as they are transported over a long time. The molten metal is cooled and solidified, to become a cast.

The mold and the cast that have been cooled by means of the system 60 for transporting and cooling the molds are transported to a shakeout machine 70. By the shakeout machine 70 a mold is taken out of a flask, the mold is crushed, and the cast is separated from the molding sand. The cast is transported to a following process as a cast product, although that is not shown in FIG. 1. The crushed molding sand is transported to a means 80 for recovering the molding sand. Then the molding sand is transported to a device 86 for cooling the molding sand, to be cooled there. The cooled molding sand is transported to the sand muller 20 through devices 87, 89 for transportation, i.e., bucket elevators, and through a device 88 for storing the molding sand, i.e., a sand bin. Water, bentonite, etc., are added to the molding sand by the sand muller 20. It is mulled and the water content is adjusted to again be transported to the molding machine 40.

The first embodiment of the present invention is now discussed with reference to a flow chart as in FIG. 3. Incidentally, the first embodiment, and the second embodiment, which is discussed below, show examples that use a tight flask molding machine that alternately molds an upper mold in an upper flask and a lower mold in a lower flask.

Figure 3:
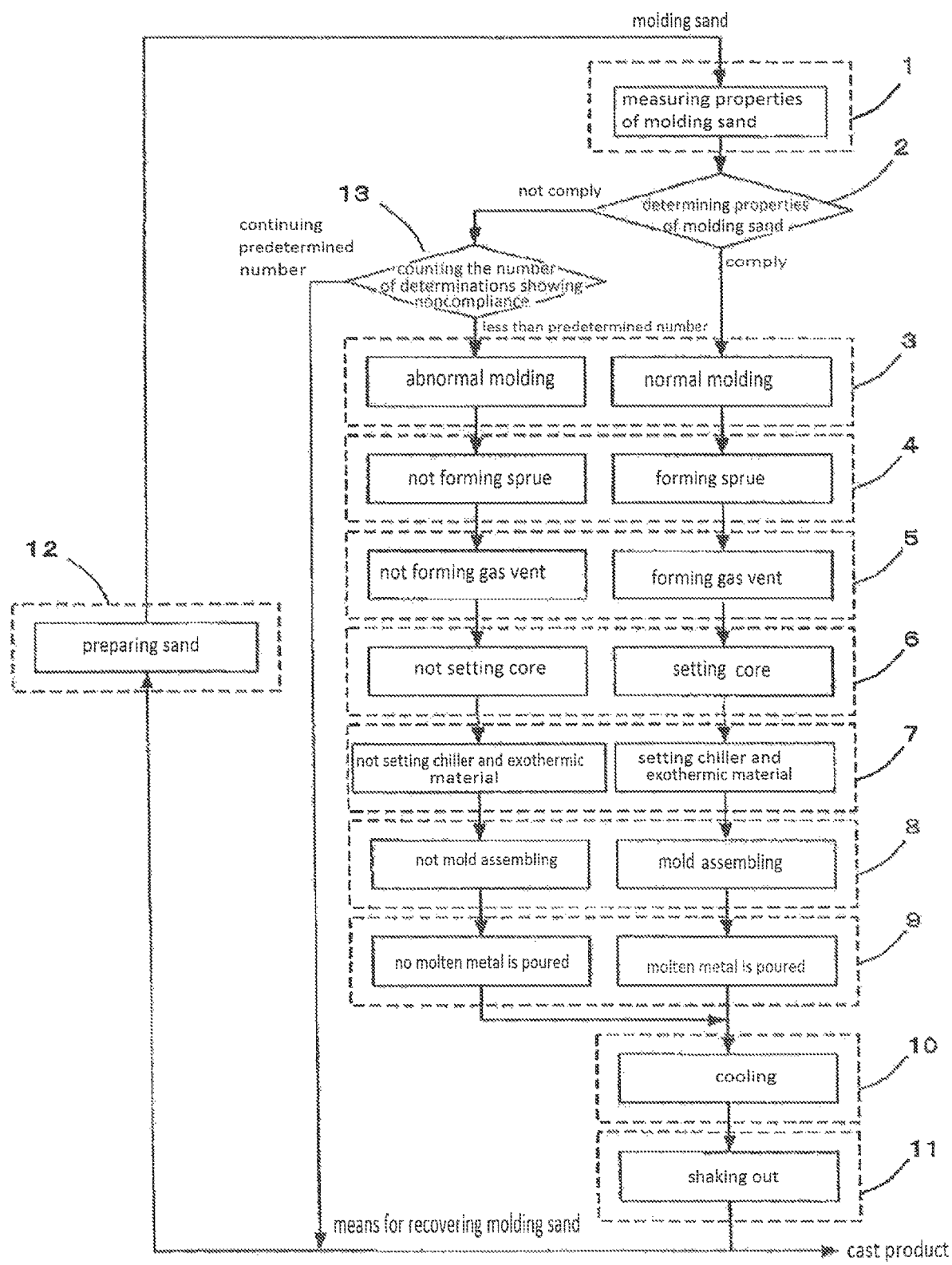
FIG. 3 is a flow chart of the first embodiment of the present invention.

As in FIG. 3, step 1 of measuring the properties of the molding sand is first carried out. In this step the properties of the molding sand as it is just before being fed to the molding machine 40 are measured by means of the device 30 for measuring the properties of the molding sand. This operation is discussed now in detail. In this embodiment the molding sand to be measured is sampled from the conveyor belt 24 that is located above the molding machine 40 and that supplied the molding sand to the molding machine 40. After either the upper mold or the lower mold is molded the conveyor belt 24 is actuated to supply the molding sand to the molding machine 40 at an amount that is equal to that of either the upper mold or the lower mold. For example, the molding sand for the measurement is sampled every time the molding sand that is used for the lower mold is transported by means of the conveyor belt 24, i.e., when the molding sand is supplied to the molding machine 40, to measure the properties of the molding sand. In this embodiment the compressive strength, the tensile strength, the shear strength, the water content, the permeability, the compactability, and the temperature of the molding sand are preferably measured as the properties of the molding sand.

Next, step 2 of determining if the properties of the molding sand are appropriate is carried out. In this step, for example, the controller determines whether the measured properties of the molding sand comply with predetermined properties. In this embodiment the predetermined properties are those where the compressive strength of the molding sand is within 10 to 20 N/cm$^2$, the water content of it is within 2.5 to 3.5%, and the comp actability of it is within 30 to 40%. If all of these three properties are within the above ranges, then the measured properties of the molding sand are determined to comply with the predetermined properties. If any of these three is not within the ranges, then the measured properties of the molding sand are determined to be not appropriate, i.e., do not comply with the predetermined properties.

As to the results, if it is determined that the measured properties of the molding sand comply with the predetermined properties, then a normal operation for molding is carried out in step 3 of molding. For example, the molding sand on the conveyor belt 24 is transported to the molding machine 40, while a part of the molding sand is sampled to measure the properties. The molding sand that is fed from the conveyor belt 24 to the molding machine 40 at the next turn is molded by the molding machine 40 so as to have the predetermined strength. Next, step 4 of forming a sprue is carried out. In this step a sprue is formed in the upper mold by means of the device for forming a sprue (not shown).

Next, step 5 of forming a gas vent is carried out. In this step a gas vent is formed in the upper mold by means of the device for forming a gas vent (not shown). Next, step 6 of setting the core is carried out. In this step a core is set in the upper mold or the lower mold by means of the device for setting a core (not shown), or by an operator.

Next, step 7 of setting a chiller and setting an exothermic material is carried out. In this step a chiller or an exothermic material is set in the upper mold or the lower mold by means of the device for setting a chiller and setting an exothermic material (not shown), or by an operator. Next, step 8 of a mold assembly is carried out. In this step, the upper mold and the lower mold are assembled by means of the device for the mold assembly (not shown).

Next, step 9 of pouring is carried out. In this step molten metal is poured by means of the pouring machine 52 into the mold that has been assembled. Next, step 10 of cooling is carried out. In this step, since the mold that has received molten metal is being transported for the predetermined period, a cast in the mold is cooled.

Next, step 11 of shaking out is carried out. In this step, by means of the shakeout machine 70 a mold is taken out of a flask, the mold is crushed, and the cast is separated from the molding sand. The separated molding sand is recovered by the means 80 for recovering the molding sand so that step 12 of preparing sand is carried out. In this step a line for preparing foundry sand removes any foreign body from the recovered molding sand, cools the molding sand, mulls and adjusts the molding sand, etc., so that the molding sand can be used for molding. Since the molding sand that has been subject to the above processes is again used for molding, step 1 of measuring the properties of the molding sand is carried out.

Next, the operations are discussed that are carried out when the determination in step 2 of determining if the properties of the molding sand are appropriate shows that the measured properties of the molding sand do not comply with the predetermined properties. If they do not comply with them, then step 13 of counting the number of determinations showing noncompliance (that the measured properties do not comply with the predetermined properties) is carried out. In this step the number of determinations showing noncompliance is counted every time the properties of the molding sand are determined.

If the number of determinations showing noncompliance that is continuously counted is less than the predetermined number, abnormal molding is carried out in step 3 of molding. Incidentally, the predetermined number is set at three, by this embodiment. In this step the molding sand that is fed from the conveyor belt 24 to the molding machine 40 at the next turn, is used to be abnormally molded. The wording "be abnormally molded" means molding so that the strength of the mold becomes less than that of a mold that is molded by using molding sand whose properties comply with the predetermined properties.

None of step 4 of forming the sprue, step 5 of forming the gas vent, step 6 of setting the core, or step 7 of setting a chiller and an exothermic material, is carried out. Thus, next, step 8 of the mold assembly is carried out. No step 9 of pouring is carried out. Next, step 10 of cooling and step 11 of shaking out are carried out. Incidentally, when no molten metal is poured into the mold, no cast product exists in the mold. Thus no cast is cooled. Thus in step 10 of cooling only the mold is transported for the predetermined period.

Next, the operations are discussed that are carried out when the number of determinations showing noncompliance becomes the predetermined number (three times in this embodiment) in step 13 of counting the number of determinations showing noncompliance. In this case the amount of the molding sand that is estimated to have the same properties (estimated not to comply with the predetermined properties), from the molding sand to be fed from the conveyor belt 24 to the molding machine 40, is recovered by the means 80 for recovering the molding sand without being molded. About the amount of the molding sand that is estimated to have the same properties and that is recovered by the means 80 for recovering the molding sand without being molded, none of step 1 of measuring the properties of the molding sand, step 2 of determining the properties of the molding sand, or step 13 of counting the number of determinations showing noncompliance, is carried out. It is recovered by the means 80 for recovering the molding sand, to be passed to step 12 of preparing sand. Incidentally, the amount of the molding sand that is estimated to have the same properties may be, for example, the amount of the molding sand that has been mulled at the same batch by the sand muller 20. Alternatively, it may be the amount of the molding sand that has been simultaneously stored in the device 26 for storing the molding sand (a sand hopper). The device 26 is provided above the conveyor belt 24 that feeds the molding sand to the molding machine 40.

Figure 4:
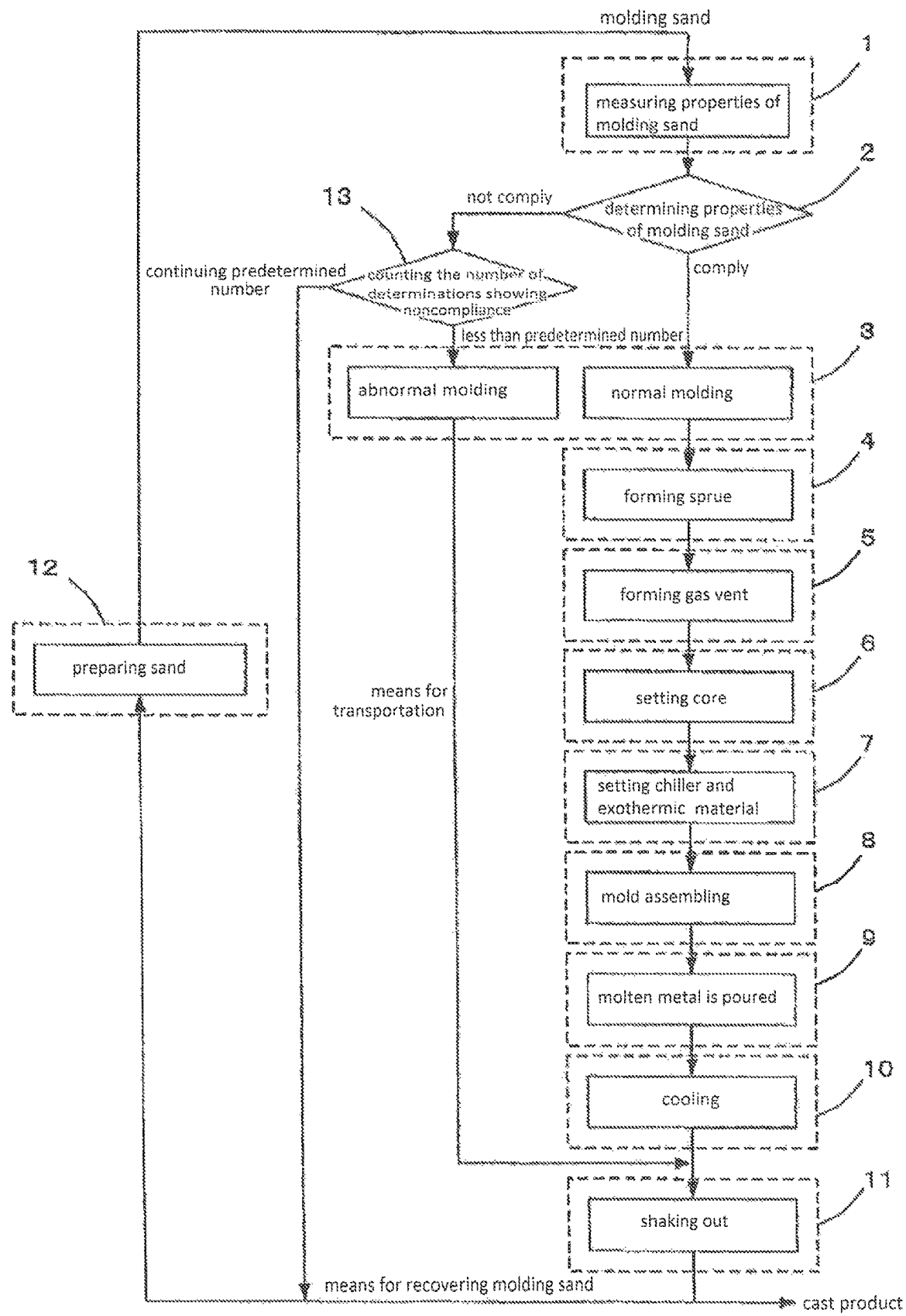
FIG. 4 is a flow chart of the second embodiment of the present invention.

Next, the second embodiment of the present invention is discussed with reference to the flow chart of FIG. 4. The point that is different from the first embodiment is now discussed. By the second embodiment, as in FIG. 4, if the number of determinations showing noncompliance that is continuously counted is less than the predetermined number (three times in this embodiment), the above-mentioned abnormal molding is carried out in step 3 of molding. This step is the same as that of the first embodiment. However, the mold is transported by a transporting means without molten metal being poured into it. At the next step, step 11 of shaking out is carried out. In this step, an upper mold is taken out of the upper flask and a lower mold is taken out of the lower flask. These operations are alternately carried out. Since no molten metal has been poured, no cast exists. This is the difference from the first embodiment. The other operations are the same as those of the first embodiment.

By the first and second embodiments of the present invention, step 1 of measuring the properties of the molding sand as it is just before being fed to the molding machine 40, and step 2 of determining if the properties of the molding sand comply with predetermined properties, are carried out. If the determination shows that the properties of the molding sand do not comply with the predetermined properties, then a mold is molded to have less strength than that of a mold that is molded by using molding sand whose properties do comply with the predetermined properties. By this configuration, energy can be advantageously saved, since a mold that may have a defect is molded by using less energy. For example, since the pressure of a hydraulic cylinder to squeeze the molding sand for molding can be low, power to be used by a hydraulic pump can be reduced.

By the first embodiment of the present invention, if the determination shows noncompliance, then the mold that is molded to have less strength than that of a mold that is molded by using molding sand whose properties do comply with the predetermined properties is assembled, but no molten metal is poured into it. By this configuration, since a cast product that has a casting defect is prevented from being produced during this stage, a possibility that a cast product has a casting defect can be advantageously decreased. Further, secondary materials for casting (for example, a core, a chiller, and an exothermic material) that would otherwise be wasted can be advantageously saved and energy for melting metal can also be advantageously saved.

By the second embodiment of the present invention, if the determination shows noncompliance, then the mold that is molded to have less strength than that of a mold that is molded by using molding sand whose properties do comply with the predetermined properties is transported without a sprue being formed, or without a gas vent being formed, without a core being set, without a chiller or an exothermic material being set, or without being assembled, or without molten metal being poured. It is to be shaken out in the next step. By this configuration, the mold that is abnormally molded is passed to step 11 of shaking out, i.e., through a different route that skips step 4 of forming the sprue through step 10 of cooling. Thus spaces for transporting that are to be used by molds that are normally molded can be advantageously prevented from being occupied by molds that are abnormally molded. Further, secondary materials for casting and energy to be consumed for melting metal can be advantageously saved.

By the first and second embodiments of the present invention, step 1 of measuring the properties of the molding sand as it is just before being fed to the molding machine 40, and step 2 of determining if the properties of the molding sand comply with predetermined properties, are carried out. If the results that show that the measured properties of the molding sand do not comply with the predetermined properties continue at the predetermined cycles, then the amount of the molding sand that is estimated to have the same properties, from the molding sand that is thereafter transported, is recovered by the means 80 for recovering the molding sand without being molded, so as to be passed to step 12 of preparing sand. By this configuration, since no mold that has a casting defect is produced, the possibility of a casting defect can be advantageously decreased.

By the first and second embodiments of the present invention, when the properties of the molding sand as it is just before being fed to the molding machine 40 are measured, the properties of the molding sand include the compressive strength, the tensile strength, the shear strength, the water content, the permeability, the compactability, and the temperature of the molding sand. However, just some features that are selected from the above-listed features may be measured.

As discussed above, the abnormal molding in the first and second embodiments of the present invention may be carried out so that the strength of the mold is less than that of a mold that is molded by using molding sand whose properties do comply with the predetermined properties. However, that mold preferably has a strength that is enough to withstand any force caused by the transportation.

The reason for the above preference is now discussed. No molten metal is poured into the mold that has been abnormally molded. This is because no cast product is produced by that mold. Thus the strength that is required for a mold that has been normally molded is not needed. Thus the strength of that mold may be the lowest in so far as it can be transported (i.e., no mold breaks or falls from a flask [an upper flask or a lower flask] during the transportation). By so doing, energy (e.g., power for the hydraulic pump) for molding can be saved. A condition to mold a mold that has the strength that is enough to withstand any force caused by the transportation may be, for example, one where a force for squeezing by a jolt squeeze molding machine is reduced to one-half of the normal force where the molding sand is not jolted. A force for squeezing by an air flow and press molding machine is reduced to one-half of the normal force where there is no flowing air. The lowest strength of a mold in so far as it can be transported may be, for example, a compressive strength of 2 to 6 N/cm$^2$.

By the first and second embodiments of the present invention, in step 13 of counting the number of determinations, different operations are carried out depending on whether the number of determinations showing noncompliance that is continuously counted is less than the predetermined number. The first and second embodiments set the predetermined number as three, but the number is not limited to three. It is preferably three, four, or five. If it were to be one or two, then the molding sand that has adhered to the device 26 for storing the molding sand for a long time and whose properties have changed would be possibly supplied to the conveyor belt 24, which supplies the molding sand to the molding machine 40. The device 26 for storing the molding sand is provided above the conveyor belt 24. If the determined number were to be six or more, then abnormal molding would have been carried out at least five times. Thus extra energy would be consumed for step 3 of molding and the subsequent steps.

By the first and second embodiments of the present invention, in step 2 of determining the properties of the molding sand, if the results show that the measured properties of the molding sand do not comply with the predetermined properties, then step 13 of counting the number of determinations showing noncompliance is next carried out. However, the present invention is not limited to this procedure. If the results show that the measured properties of the molding sand do not comply with the predetermined properties, abnormal molding may be always (i.e., at every cycle) carried out. Since abnormal molding is carried out every time the results show noncompliance, step 13 of counting the number of determinations showing noncompliance is not needed.

By the first and second embodiments of the present invention, as a molding machine, the tight flask molding machine 40, which alternately molds an upper mold in an upper flask and a lower mold in a lower flask, is used. The present invention is not limited to this configuration. It can be applied to a configuration where a flaskless molding machine is used, so that upper and lower molds are simultaneously molded, so that the upper and lower molds are assembled, so that the molds are extracted from the flasks, and so that only the molds are carried out of the flaskless molding machine.

By the present invention, the method may comprise a step of storing data on the properties of the molding sand that has been measured by means of the device 30 for measuring the properties of the molding sand as the data that relates to a cast product that is manufactured by pouring molten metal into a mold that is molded by using that molding sand. For example, the data on the properties of the molding sand that have been measured by the device 30 for measuring the properties of the molding sand are transmitted from the device 30 for measuring the properties of the molding sand to the controller (not shown) to be stored by the controller as data that relate to the molding sand. Next, the data on the properties of the molding sand are linked to the mold that has been molded by using that molding sand. In the controller the stored data on the properties of the molding sand are linked to the cast product that has been produced by that mold. Thus the data on the properties of the molding sand can be stored as information that relates to the cast product.

The data on the molding conditions of the mold may be also stored as information that relates to the cast product. The molding conditions include the squeezing pressure, but they are not limited to the above. Data on the molding conditions that are actually used by the molding machine 40 with respect to each mold are transmitted to the controller to be stored there.

Then, the quality of the cast product is inspected. If the quality does not meet the requirements of predetermined quality, then the mold may possibly have a defect. Since the properties of the molding sand and the molding conditions of the mold are stored as information that relates to the cast product, the process of manufacturing can be traced.

For example, the controller may modify the predetermined properties that are used at step 2 of determining the properties of the molding sand, depending on the result of the tracing, by using the properties of the molding sand. If cast products whose qualities do not comply with the predetermined quality are continuously produced, even though molten metal whose properties do comply with the predetermined properties is used, the predetermined properties may be modified to exclude the properties of the molding sand that is used for molding the mold that is used for that cast product. In this way, since the properties of the molding sand can be fed back based on the quality of a cast product, reliable predetermined properties can be set. Incidentally, by feeding back the molding conditions reliable predetermined properties also can be set.

In the method for managing the casting process the properties of the molding sand that are measured and used for a determination may be one or more features that are selected from the group of compressive strength, tensile strength, shear strength, water content, permeability, compactability, and the temperature, of the molding sand. If the properties of the molding sand that are measured and used for the determination are compressive strength, water content, and compactability, then the following advantages are obtained. The compressive strength, water content, and compactability can be easily adjusted compared with the other features. They can be adjusted by changing the amount of water or bentonite that is added to the sand muller 20. Thus a great advantage can be obtained wherein the properties of the molding sand can be adjusted to comply with the predetermined properties. If all seven features listed above are measured and used for the determination, an advantage can be obtained from the standpoint of the measurement and the determination. However, the cycle time may become longer. In contrast, if only three features, i.e., compressive strength, water content, and compactability, are measured and used, the cycle time does not become longer than necessary. Proper measurements, determinations, and adjustments can be achieved. Incidentally, the properties of the molding sand that are used for the determination may be one or more that are selected from the measured properties of the molding sand.

The reference signs used in the present specification and the drawings are as follows:

1 The step of measuring the properties of the molding sand
2 The step of determining the properties of the molding sand
3 The step of molding
4 The step of forming the sprue
5 The step of forming the gas vent
6 The step of setting the core
7 The step of setting a chiller and an exothermic material
8 The step of the mold assembly
9 The step of pouring
10 The step of cooling
11 The step of shaking out
12 The step of preparing sand
13 The step of counting the number of determinations showing noncompliance
20 The sand muller
22a, 22b The conveyor belt
23 The hopper
24 The conveyor belt (the sand feeder)
26 The device for storing the molding sand
30 The device for measuring the properties of the molding sand
40 The molding machine
52 The pouring machine
54 The device for pretreatment to pour molten metal into a mold
60 The system for transporting and cooling the molds
70 The shakeout machine
80 The means for recovering the molding sand
86 The device for cooling the molding sand
87, 89 The bucket elevator
88 The device for storing the molding sand (the sand bin)
100 The green sand casting system

The invention claimed is:

1. A method for managing a casting process based on properties of molding sand comprising the steps of:
   measuring the properties of the molding sand just before the molding sand is supplied to a molding machine;
   determining that the measured properties of the molding sand do not comply with predetermined properties associated with avoiding a casting defect;
   continuously counting a number of determinations showing noncompliance with said predetermined properties;
   when the number of determinations is less than a predetermined number, molding a mold, and shaking out the mold that has been molded when the measured properties do not comply with the predetermined properties;
   when the number of determinations reaches a predetermined number, adjusting properties of the molding sand to comply with predetermined properties,
   molding a mold when the measured properties do comply with the predetermined properties, the mold having strength that is suitable for the casting process;
   pouring molten metal into the mold that is formed at the step of forming a mold when the measured properties comply with the predetermined properties;
   cooling a cast product in the mold into which the molten metal has been poured;
   shaking out the cooled mold in which a cast product is held into the cast product and molding sand; and
   molding a mold when the measured properties do not comply with the predetermined properties, the mold having less strength than that of the mold that is molded when the measured properties do comply with the predetermined properties.

2. The method for managing the casting process based on the properties of the molding sand of claim 1, wherein the properties of the molding sand include one or more features that are selected from a group of compressive strength, tensile strength, shear strength, water content, permeability, compactability, and a temperature, of the molding sand.

3. The method for managing the casting process based on the properties of the molding sand of claim 1, wherein the mold that has been molded when the measured properties do not comply with the predetermined properties is assembled at a step that comes after a step of molding, and wherein no molten metal is poured into the assembled mold.

4. The method for managing the casting, process based on the properties of the molding sand of claim 1, wherein the mold that has been molded when the measured properties do not comply with the predetermined properties is transported after being molded and is shaken out without molten metal being poured.

5. The method for managing the casting process based on the properties of the molding sand of claim 1, further comprising a step of storing data on the measured properties of the molding sand as data on a cast product that has been produced by pouring molten metal into a mold that is molded by using that molding sand, if by the step of determining it is found that the measured properties do comply with the predetermined properties.

6. The method for managing the casting process based on the properties of the molding sand of claim 5, wherein, in the step of storing data on the measured properties, data on molding conditions by which the molding sand is molded are also stored as data on the cast product.

7. The method for managing the casting process based on the properties of the molding sand of claim 5, wherein the properties of the molding sand include one or more features that are selected from a group of compressive strength, tensile strength, shear strength, water content, permeability, compactability, and a temperature, of the molding sand,
   wherein, if in the step of determining it is found that one of the selected features exceed predetermined ranges, then the properties of the molding sand are determined not to comply with the predetermined properties, and
   wherein the method further comprises a step of modifying the predetermined ranges that are used in the step of determining based on the properties of the molding sand that are stored as data on the cast product, if quality of the cast product that has been produced does not comply with predetermined quality.

8. The method for managing the casting process based on the properties of the molding sand of claim 1, wherein the properties of the molding sand include compressive strength, water content, and compactability,
   wherein in the step of determining if the compressive strength, or the water content, or the compactability exceeds a predetermined range, then the measured properties of the molding sand are determined not to comply with predetermined properties.

9. A method for managing a casting process based on properties of molding sand comprising the steps of:

measuring the properties of the molding sand just before the molding sand is supplied to a molding machine;

determining if the measured properties of the molding sand comply with predetermined properties so as to then switch between a step of molding a mold when the measured properties do comply with the predetermined properties and a step when the measured properties do not comply with the predetermined properties;

molding a mold when the measured properties do comply with the predetermined properties, the mold having strength that is suitable for the casting process;

pouring molten metal into the mold that is formed at the step of forming a mold when the measured properties do comply with the predetermined properties;

cooling a cast product in the mold into which the molten metal has been poured;

shaking out the cooled mold in which a cast product is held into the cast product and molding sand;

counting a number of determinations showing noncompliance, when the measured properties do not comply with the predetermined properties, which number is continuously counted, to see if the number reaches a predetermined number;

passing the molding sand that is estimated to have the same properties to a step of preparing sand, where the sand is mulled without being molded, if the counted number reaches the predetermined number;

molding a mold, the mold having less strength than that of the mold that is molded when the measured properties do comply with the predetermined properties, if the counted number does not reach the predetermined number; and shaking out the mold that has been molded when the measured properties do not comply with the predetermined properties.

* * * * *